United States Patent [19]

Kato et al.

[11] Patent Number: 4,581,706
[45] Date of Patent: Apr. 8, 1986

[54] METHOD AND APPARATUS FOR TESTING A JOINT

[75] Inventors: Syuzo Kato, Narashino; Tutomu Takahashi, Sakura; Hiroshi Ishimura, Narashino; Sotozi Hiramoto, Chiba, all of Japan

[73] Assignee: Hitachi, Ltd., Tokyo, Japan

[21] Appl. No.: 460,657

[22] Filed: Jan. 24, 1983

[30] Foreign Application Priority Data

Jan. 25, 1982 [JP] Japan .................................. 57-8913
Oct. 8, 1982 [JP] Japan ................................ 57-176122

[51] Int. Cl.⁴ ............................................. G06F 15/46
[52] U.S. Cl. .................................. 364/506; 358/106; 356/394
[58] Field of Search ...................... 364/506, 507, 477; 356/394; 358/106, 101; 382/28

[56] References Cited

U.S. PATENT DOCUMENTS

| | | | |
|---|---|---|---|
| 4,156,231 | 5/1979 | Edamatsu et al. | 382/28 |
| 4,290,698 | 9/1981 | Milana | 356/394 X |
| 4,364,113 | 12/1982 | Sengebusch et al. | 364/507 |
| 4,390,954 | 6/1983 | Manning | 364/477 |
| 4,403,294 | 9/1983 | Hamada et al. | 364/507 |
| 4,432,013 | 2/1984 | Miller et al. | 358/106 |
| 4,433,385 | 2/1984 | De Gasperi et al. | 358/106 X |

Primary Examiner—Edward J. Wise
Attorney, Agent, or Firm—Antonelli, Terry & Wands

[57] ABSTRACT

A joint of a member joined by joining apparatus is tested by detecting an area of the joint and checking if the area has a predetermined value or not. A test apparatus includes an imaging device for imaging the joint on an image plane and converting the image to an electric signal and a processor for extracting the area of the joint from the electric signal from the imaging means to test the joint.

27 Claims, 33 Drawing Figures

FIG. 1
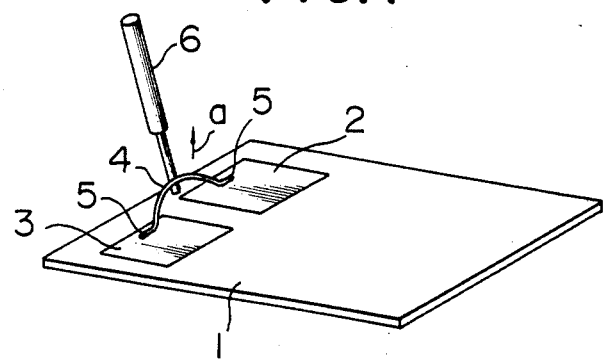
FIG. 2
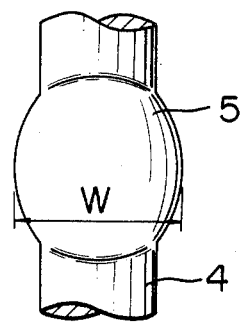
FIG. 3
FIG. 4
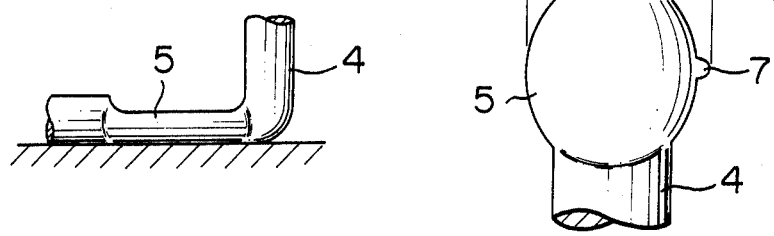

METHOD AND APPARATUS FOR TESTING A JOINT

The present invention relates to method and apparatus for testing a joint, such as a strength of a joint joined by joining means, and it is particularly adaptable to test a joint between an element of a semiconductor integrated circuit and a lead wire or between the lead wire and a post where the elements of the semiconductor integrated circuit or the element and the post are interconnected by the lead wire by a wire bonding apparatus.

The interconnection between the semiconductor integrated circuit elements mounted on a substrate or between the semiconductor integrated circuit element and the post formed on the substrate is usually made by a lead wire made of aluminum by utilizing an ultrasonic wave bonding technique. FIG. 1 shows the interconnection between the semiconductor integrated circuit element mounted on the substrate and the post, in which numeral 1 denotes the substrate, numeral 2 denotes the semiconductor integrated circuit element mounted on the substrate 1, numeral 3 denotes the post and numeral 4 denotes the lead wire for electrically connecting the semiconductor integrated circuit element 2 and the post 3. The lead wire 4 is usually made of aluminum. In such a structure, a test for the joint 5 between the semiconductor integrated circuit element 2 or the post 3 and the lead wire 4 is effected by pulling the lead wire 4 by a pulling device 6 with a predetermined pulling force and watching whether the lead wire 4 maintains the connection or not under such a condition. If the joint 5 is destroyed by the predetermined pulling force, it fails the test, and if the joint 5 is maintained it passes the test. The magnitude of the pulling force may be experimentally determined.

This type of test for the joint 5 imparts an external force to the lead wire 4 to physically change it and hence imparts a force to the joint 5. Accordingly, adverse affects such as deformation of the lead wire 4, damage of the lead wire 4 and affect to the joint 5 are encountered, which lead to reduction of a yield.

FIGS. 2 and 3 show a plan view and a side elevational view of the joint 5 of the lead wire 4 formed by an ultrasonic wave wire bonding apparatus. As shown, the lead wire 4 is plastically deformed by the ultrasonic wave bonding. The plastically deformed portion is the joint 5. A maximum deformation width W of the joint 5 varies from work to work. It has been known that there is a correlation between the maximum deformation width W and a tensile strength. Thus, it may be possible to determine the strength of the joint 5 indirectly by measuring the maximum deformation width W of the joint 5 to determine if it has a predetermined width or not so that the joint 5 can be tested by a non-contact method without imparting an external force to the lead wire 4. This method can resolve the problems encountered in the prior art method. However, the joint 5 shown in FIGS. 2 and 3 is an ideal joint and the actual joint 5 has one of various shapes. For example, if the joint 5 has a projection 7 at a center thereof as shown in FIG. 4, even if the maximum deformation width W has the predetermined width, it does not have the predetermined tensile strength and the joint is destroyed in the pulling test.

It is an object of the present invention to provide method and apparatus for testing a joint in a non-contact method without imparting an external force to the joint, with a high precision of test.

In order to achieve the above object, in accordance with a feature of the present invention, an area of the joint is a subject to be tested.

The inventors of the present invention prepared many samples of joint, tested them for the tensile strength and collected data. According to the experiment, for those samples having joint shapes as shown in FIG. 2, there exists a correlation between the maximum deformation width and the tensile strength. However, for those samples which have other special shapes as represented by FIG. 4, the correlation is extremely weak or zero. Thus, the inventors reached a conclusion that, for the sample such as shown in FIG. 4, the extremely projecting projection 7 of the joint 5 has a great influence to the maximum deformation width W of the joint 5 but does not contribute to the enhancement of the joining force or the tensile strength. Thus, the inventors studied the joints 5 of those samples which have the weak or no correlation between the maximum deformation width W and the tensile strength, that is, those having the extremely projecting projections 7. As a result, the inventors reached a conclusion that a ratio of an area of the projection 7 to a total area of the joint 5 is very small. They measured the areas of the joints and the tensile strengths for many samples. The measurements are summarized in FIG. 5. The samples were prepared by the ultrasonic wave bonding technique under the following condition. The wire bonding apparatus used is of ultrasonic wave type having a maximum oscillation output of 20 watts, made by Orthodyne Electronics, USA, which is designed for a thick wire, has a wedge made of a super alloy and has a groove. A joint surface is an aluminum evaporated film, the lead wire is made of aluminum of 99.99% purity; having a diameter of 300 μm and a tensile strength of 350 grams. In FIG. 5, an ordinate represents a tensile strength (in grams) when the lead wire 4 is pulled normally to the substrate 1 and an abscissa represents an area increase factor (in percent). The area increase factor is calculated in the following manner. Referring to FIG. 6, the area increase factor Wa is given by $$Wa = \frac{\Sigma l_x - l_{mini} \cdot l_t}{l_{mini} \cdot l_t} \times 100 \, (\%) \qquad (1)$$

where $l_{mini}$ is a diameter of the lead wire 4, $l_t$ is a length of that portion of the joint 5 which has a width which is no less than 1.2 times as wide as the diameter $l_{mini}$ of the lead wire 4, and $\Sigma l_x$ is an area of that portion, that is, a hatched area.

In the formula (1), $l_{mini} \cdot l_t$ represents an area of the lead wire 4 per length $l_t$. The area increase factor Wa indicates a degree of area increase after the joint, of the $l_t$ portion of the lead wire 4. The length $l_t$ is selected to 1.2 $l_{mini}$ because of an assumption that a characteristic of the joint 5 concentrates in the center thereof.

As seen from FIG. 5 which summarizes the measurements, there exists a correlation between the tensile strength and the area increase factor $W_a$. According to the experiment, the peel-off of the joint 5 is often observed when the area increase factor Wa is less than 30%. When the area increase factor Wa is no less than 30%, most joints are broken. When they are broken, the tensile strength depends on not the strength of the joint 5 but the strength of the plastically deformed lead wire 4. In a high area increase factor region, the tensile strength gradually decreases as the area increase factor $W_a$ increases.

This relation is utilized in the present invention and the area of the joint 5 is selected as the subject for the test of the joint 5. A range of pass for the test of the joint 5 joined under the same condition as described above is set to the area increase factor $W_a$ of the joint 5 of 30%–55%. The range varies depending on a particular tensile strength of the joint 5 and a desired yield. After the joined of the lead wire 4, the area of the joint 5 is measured and the area increase factor $W_a$ is calculated in accordance with the formula (1). If the area increase factor $W_a$ is within the range of 30%–55%, it passes the test, otherwise it fails the test.

In this manner, the joint 5 can be tested in non-contact method without imparting an external force. In this method, if the joint 5 has a peculiar shape as represented by FIG. 4 and does not have the predetermined tensile strength, it does not pass the test. Thus, the test accuracy is improved. As described above, the ratio of the area of the projection 7 to the total area of the joint 5 is very small. Accordingly, the influence by the projection 7 is negligible in calculating the area increase factor $W_a$ in accordance with the formula (1).

While it has been explained to use the formula (1) in the test of the joint 5, the area increase factor $W_a$ may be calculated based on the total area of the joint 5. Referring to FIG. 7, an area increase factor $W_a'$ is given by $$W_a' = \frac{\Sigma l_x' - l_{mini} \cdot l_t'}{l_{mini} \cdot l_t'} \times 100 \, (\%) \quad (2)$$

or $$W_a' = \frac{\Sigma l_x'}{l_{mini} \cdot l_t'} \times 100 \, (\%) \quad (3)$$

where $\Sigma l_x'$ is the total area of the joint 5, and $l_t'$ is the length of the joint 5.

Alternatively, an area increase factor for a hatched area shown in FIG. 8 corresponding to 1.2 $l_{mini} \cdot l_t$ or $l_{mini} \cdot l_t$ may be used, or a reciprocal of one of those may be used.

The decision of the test may be made by an absolute value of the area of the joint 5. A maximum allowable area and a minimum allowable area are preset, the area of the joint 5 is compared with them and the decision of the test is made whether the area is within the preset range.

Many decision conditions may be considered and the present invention is not limited by the decision methods.

In this manner, the test accuracy for the joint is remarkably improved. If a further improvement of the test accuracy is desired, the shape of the joint may be determined. According to FIG. 5, a peculiar phenomenon occurs in that the vertical tensile strength is 160 grams while the area increase factor $W_a$ is within the predetermined range as represented by S in FIG. 5. FIG. 9 shows a shape of the joint 5 thereof. As seen from FIG. 9, the joint 5 is unbalanced in shape with respect to a center line C of the lead wire 4. A portion on the left of the center line C is plastically deformed very little while a right portion is plastically deformed to a great extent. Such a shape is actually produced depending on a contact condition of the lead wire 4 and a tool for urging the lead wire 4 to a contact surface when the lead wire 4 is joined. When the joint 5 has such a shape, the tensile strength thereof is reduced.

Thus, in addition to the area increase factor of the joint 5, the shape of the joint 5, that is, an unbalance factor (called a strain factor) relative to the center line C of the lead wire 4 is also used as a check item. FIG. 10 shows a summary of measurements of the tensile strength (in grams) for samples which were intentionally prepared to have an unbalance relative to the center line C. Other conditions for preparing the samples are same as those of FIG. 5 and the samples have the area increase factors within the allowable range. In FIG. 10, an ordinate represents the vertical tensile strength and an abscissa represents a strain factor $W_c$ (%). The strain factor $W_c$ is calculated in the following manner. In FIG. 9, a left portion of that portion (hatched portion) of the joint 5 which has a width which is no less than 1.2 times as wide as the width $l_{mini}$ of the lead wire 4, on the left of the center line C is represented by $\Sigma A$, and a right portion is represented by $\Sigma B$. (Assume that $\Sigma A < \Sigma B$) Thus, the strain factor $W_c$ is given by $$W_c = \left| \left( 1 - \frac{\Sigma A}{\Sigma B} \right) \right| \times 100 \, (\%) \quad (4)$$

As seen from FIG. 10, the tensile strength of the joint 5 gradually decreases as the strain factor exceeds 25% even if the area increase factor is within the allowable range. Taking this relation into consideration, the joint 5 having the strain factor of no larger than 20% is passed for the test. This range varies depending on a particular tensile strength and a desired yield, like the range for the area increase factor. After the joining of the lead wire 4, the areas $\Sigma A$ and $\Sigma B$ of the joint 5 are measured or calculated and the strain factor $W_c$ is calculated in accordance with the formula (4). If the strain factor $W_c$ is no larger than 20%, it passes the test, otherwise it fails the test. The check by the strain factor may be effected either after or before the check by the area increase factor.

By adding the strain factor to the check conditions, the test accuracy is more improved.

While it has been explained to use the formula (4) to calculate the strain factor, many other alternatives may be considered as is the case of the calculation of the area increase factor. For example, an area ratio after the reduction of the area of the lead wire 4 may be used. The present invention is not limited to those calculation methods.

An apparatus of the present invention includes imaging means and processing means. The joint is imaged by the imaging means. As seen from the above description, the joint is very fine. Thus, it is desirable from a precision stand point to image the joint through magnifying means such as a lens. The magnifying means may be separate from the imaging means but it is preferable from the construction stand point that the imaging means is equipped with the magnifying means. The imaging means converts an image focused on an image plane to an electric signal to provide video information, and it may be a television camera having an imaging tube which converts the image focused on the image plane to the electric signal by deflecting and focusing electron beams emitted from an electron gun by a coil, or a solid-state television camera having a solid-state imaging device instead of the imaging tube. It sequentially scans a number of lines on the image plane to convert the image to the electric signal.

The processing means receives the video information from the imaging means, extracts the area of the joint from the video information and checks the joint based on the extracted area of the joint. The processing means is conveniently of digital processing system. To this end, the processing means has digitizing means for digitizing the video information from the imaging means so that the output of the digitizing means is processed. The output of the digitizing means may be directly processed but it is advisable from the construction stand point to temporarily store the digitized video information in memory means and process the information stored in the memory means. A main portion of the processing means for making the decision is a microcomputer although other arithmetic and processing means having similar functions may be used. In the decision process, the arithmetic and processing means may sequentially read out the contents of the memory means or the video memory means which temporarily stores the video information, or data preparing means which prepares information necessary for the decision based on the information stored in the video memory means may be provided and the arithmetic and processing means makes the decision based on the information from the data preparing means. In the latter case, the processing speed can be further increased.

The present invention will be apparent from the folloiwng description taken in conjunction with the accompanying drawings, in which:

FIG. 1 illustrates a prior art test method;

FIG. 2 shows a plan view of a joint;

FIG. 3 shows a side elevational view of the joint of FIG. 2;

FIG. 4 shows a plan view of another joint;

Figure 11:
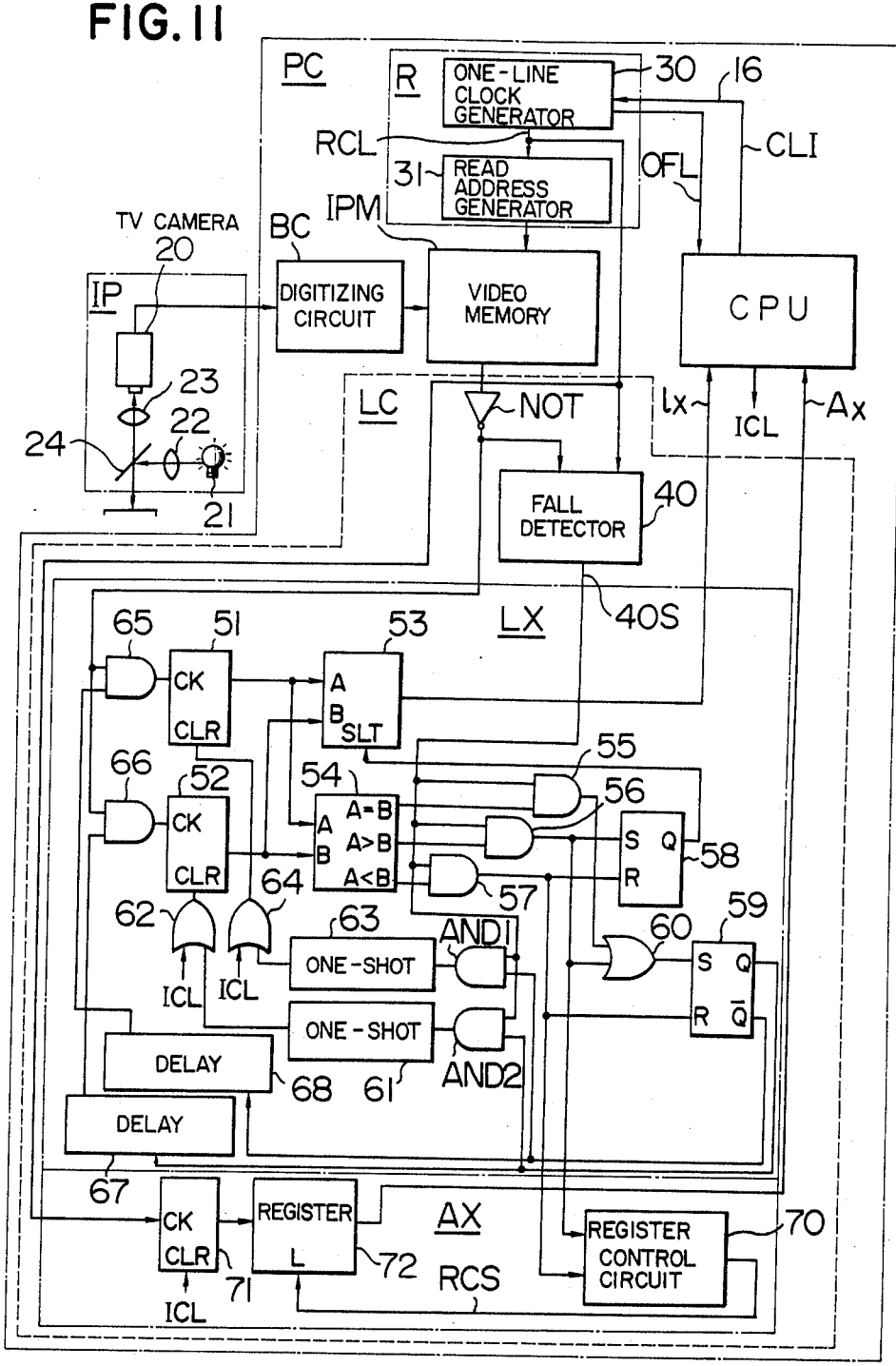
FIG. 11 shows a block diagram of one embodiment of the present invention.
Figure 12:
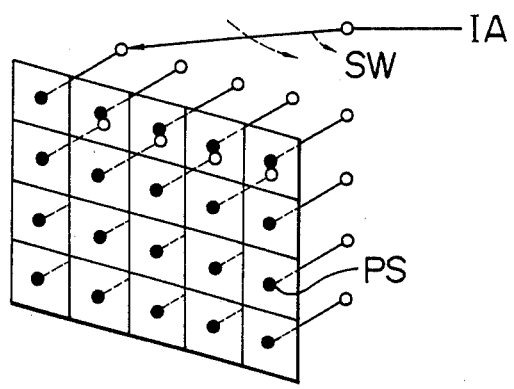
FIG. 12 illustrates a principle of a television camera.
Figure 13:
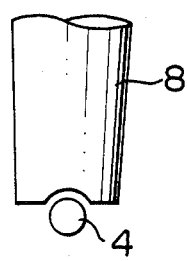
FIG. 13 shows a shape of a groove of a bonding apparatus.
Figure 14:
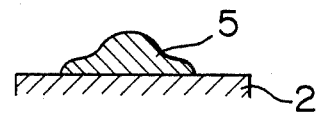
FIG. 14 shows a sectional view of a joint.
Figure 15:
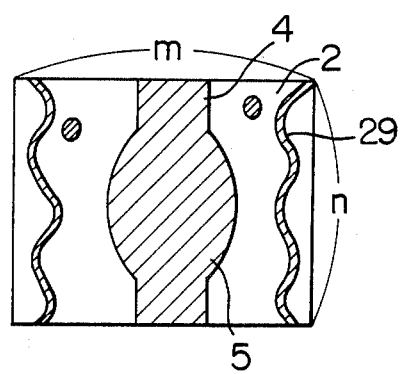
FIG. 15 shows an example of image.

FIG. 11 shows one embodiment of the apparatus of the present invention. IP denotes imaging means and PC denotes processing means. A main portion of the imaging means IP is a television camera (hereinafter referred to as a TV camera) 20. In the present embodiment, the TV camera 20 is a solid-state TV camera having a solid-state imaging device. A principle of operation thereof is illustrated in FIG. 12. The solid-state imaging device is a highly integrated circuit device comprising a number of, for example, 244 in vertical by 320 in horizontal photosensors PS and a switching circuit SW. An image focused on an imaging plane is scanned by the switch to produce an electric signal. The image plane is divided into 244×320 picture cells. The signal is taken out as a signal of the TV camera 20 through a video amplifier IA. Where the lead wire 4 is jointed by a groove-shaped tool 8 as shown in FIG. 13 which is used in an ultrasonic wave wire bonding apparatus, the plastically deformed joint has a sectional shape as shown in FIG. 14. The imaging means IP further includes an illumination source 21. A condenser lens 22 for collecting light from the illumination source 21 and directing it to an object to be imaged, an object lens 23 and a reflection mirror 24. When the light from the illumination source 24 is projected to the joint 5 having the sectional shape shown in FIG. 14 normally to the joint 5 by the reflection mirror 24, the light impinged to the joint 5 scatters and does not go into the object lens 23 and hence into the TV camera 20. Since the surface of the semiconductor integrated circuit element 2 or the post 3 to be joined is planar, the light is reflected in the direction of projection and passes through the object lens 23 into the TV camera 20. FIG. 15 shows an image of the TV camera 20 monitored. The object to be joined is the semiconductor integrated circuit element 2. The joint 5 and the lead wire 4 in the hatched area appear black and the semiconductor integrated circuit element 2 appears white. Certain portions of the semiconductor integrated circuit element, that is, unevenness in the surface, defects or wiring pattern 29 appear black.

Figure 16:
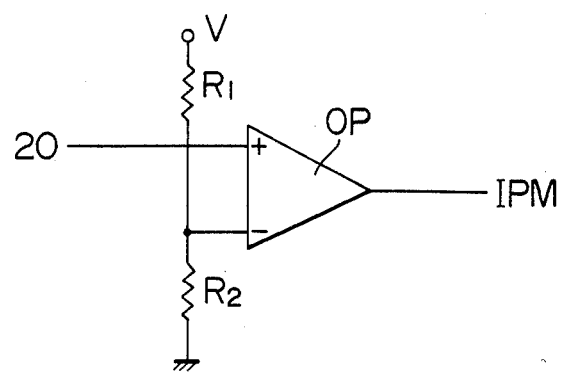
FIG. 16 shows a circuit diagram of a digitizing circuit.

The processing means PC comprises a digitizing circuit BC, a video memory IPM, a read circuit R, a data preparing circuit LC and a processor CPU. Since the output signal from the TV camera 20 is an analog signal, the digitizing circuit BC digitizes it, that is, converts it to "1" and "0" signals. FIG. 16 shows an example of the digitizing circuit BC which uses a comparator constructed by an operational amplifier OP. R1 and R2 denote a voltage divider which divides a voltage of a power supply V to produce a reference voltage which is used as a reference to discriminate the input voltage from the TV camera 20 to the "1" or "0" signal. If the input voltage from the TV camera 20 is higher than the reference voltage, the output of the operational amplifier OP and hence the output of the digitizing circuit is "1", and if it is lower than the reference voltage, the output is "0".

Figure 17:
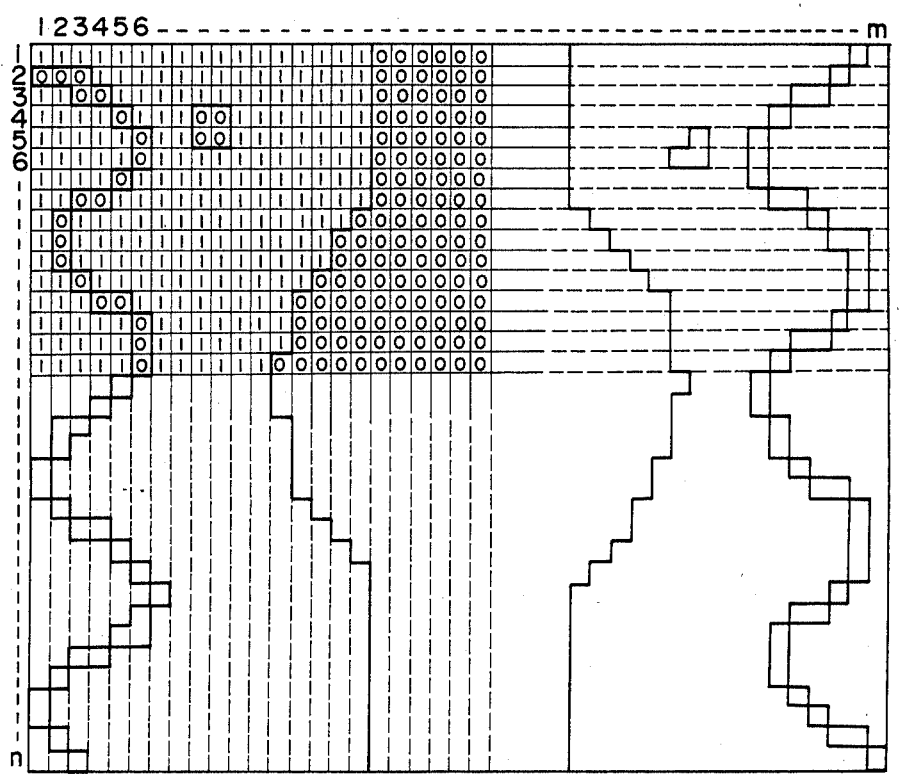
FIG. 17 shows an example of digitized image.

The video memory IPM has one-bit memories one for each of the photosensors PS of the solid-state imaging device. Assuming that the solid-state imaging device has 244 in vertical by 320 in horizontal picture cells, it has a total of 78,080 photosensors PS. Thus, the video memory IPM has a memory capacity of at least 78,080 bits, if a high precision is required, although they may be appropriately thinned to reduce the capacity of the video memory IPM. While not shown, the video memory IPM has a write circuit. When the TV camera 20 produces the output of the photosensor PS at a certain position by the action of the switching circuit SW, the memory corresponding to that photosensor PS is addressed. The "1" or "0" signal from the digitizing circuit BC, depending on the output from the TV camera 20, is written in the addressed memory. When the TV camera 20 has produced all electric signals of the image, the digitized image is temporarily stored in the video memory IPM. FIG. 17 shows a partial conceptual chart of the video memory IPM which stores the image and it corresponds to the chart of FIG. 15. In FIG. 17, each section represents each memory. The TV camera 20 produces a relatively high voltage for the portion which appears white in FIG. 15 and the output of the digitizing circuit BC for that portion is "1". The TV camera 20 produces a relatively low voltage for the black portion and the output of the digitizing circuit BC for that portion is "0". As a result, the memories of the video memory IPM store the "1" and "0" signals in a manner shown in FIG. 17. The center portion having concentrated "0" corresponds to the joint 5. The video memory IPM is a $(m \times n)$-bit memory to comply with FIG. 17 and the addresses thereof are numbered sequentially in ascending order from the left end to the right end in the top line, thence to the following line.

Figure 18:
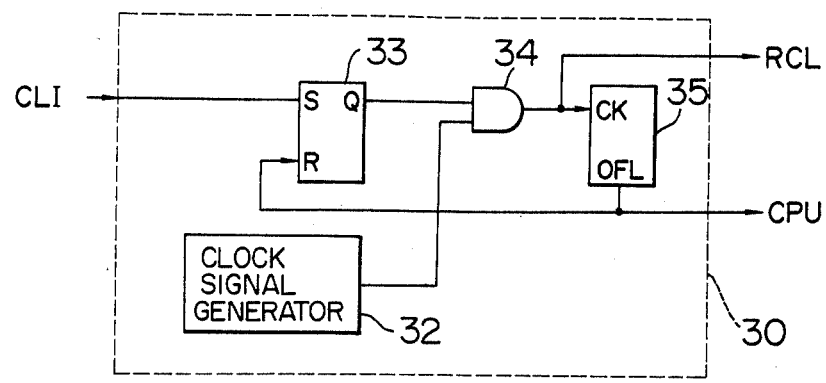
FIG. 18 shows a block diagram of a one-line clock generator.

The read circuit R sequentially reads out the contents of the video memory IPM. It reads one line at a time by a clock generation instruction signal CLI from the processor CPU. To this end, the read circuit R comprises one-line clock generator 30 and a read address generator 31. When the one-line clock generator 30 receives the clock generation instruction signal CLI, it generates m pulses corresponding to one line of image in the video memory IPM. FIG. 18 shows an example of the one-line clock generator 30. It comprises a clock signal generator 32, an RS flip-flop 33, an AND gate 34 and a counter 35. The clock signal generator 32 generates sequential pulses of a constant period. The output pulses from the clock signal generator 32 are supplied to a count terminal CK of the counter 35 through the AND gate 34. The clock generation instruction signal CLI from the processor CPU is supplied to a set terminal S of the RS flip-flop 33 so that the RS flip-flop 33 is set by the signal CLI. An output from an output terminal Q of the flip-flop 33 is supplied to a control input terminal of the AND gate 34 so that the AND gate 34 is opened while the flip-flop 33 is set. The counter 35 is a scale of $(m-1)$ counter because the video memory IPM has m bits in each line, and an output from an overflow terminal OFL is supplied to a reset terminal R of the RS flip-flop 33. The output of the AND gate 34 is supplied to the count terminal CK of the counter 35 and also supplied to the read address generator 31 as a read clock pulse RCL. Thus, when the clock generation instruction signal CLI is supplied from the processor CPU, the RS flip-flop 33 is set and the AND gate 34 is opened by the "1" output from the output terminal Q. Thus, the clock pulse from the clock generator 32 is supplied to the counter 35 through the AND gate 34 and also supplied to the read address generator 31. The counter 35 is counted up by the clock pulse. When the m-th signal is supplied, the signal is produced from the overflow terminal OFL to reset the RS flip-flop 33. As a result, the signal at the output terminal Q of the RS flip-flop 33 is "0" and the AND gate 34 is closed. The subsequent clock pulse from the clock generator 32, therefore, does not pass the AND gate 34. Thus, the circuit 30 produces m clock pulses or read clock pulses RCL for each clock generation instruction signal CLI from the processor CPU and then stops to produce the read clock pulse RCL.

The read address generator 31 receives the read clock pulse RCL from the one-line clock generator 30, sequentially addresses the video memory IPM in response to the pulse RCL and sequentially reads out the stored content. It may be an address counter. The circuit 31 attains the above fraction by incrementing the address by one each time when it receives one read clock pulse RCL. The one-line clock generator 30 generates m pulses whenever it receives the clock generation instruction signal CLI from the processor CPU. When the one-line clock generator 30 receives the first signal CLI, the read address generator 31 addresses the m bits in the first line in FIG. 17 to read out the contents stored therein. When the second signal CLI is applied to the circuit 30, the read address circuit 31 addresses the m bits in the second line to read out the contents stored therein. Similarly, whenever the clock generation instruction signal CLI is supplied from the processor CPU, the stored content of the corresponding line is read, and when the last or n-th line has been read, the circuit 31 is set to read out the first line next.

Figure 19A:
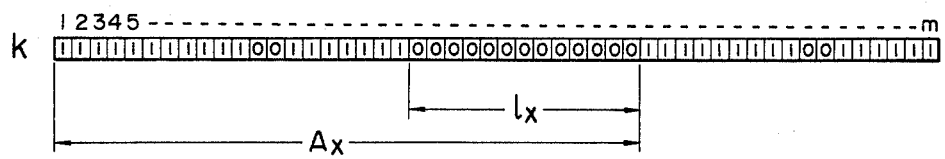
FIG. 19a and 19b show outputs from a video memory.

The data preparing circuit LC prepares the data necessary to determine the area and the condition of the joint 5, for each line of the video memory IPM in FIG. 17, based on the output from the video memory IPM. FIG. 19a shows a sample of the memory content in an arbitrary line k of FIG. 17. The data preparing circuit LC detects a joint data lx comprising the number of bits corresponding to the joint 5 and a joint end data Ax comprising the number of bits starting from the first bit and ending at the end of the joint 5, and supplies them to the processor CPU. As seen from FIG. 19a, the number of bits or the number of picture cells corresponds to the area. The data preparing circuit LC comprises a joint detector Lx for detecting the joint data lx, a joint end detector Ax for detecting the joint end data Ax and a fall detector 40 for supplying a timing signal to the circuits Lx and Ax.

Figure 19B:
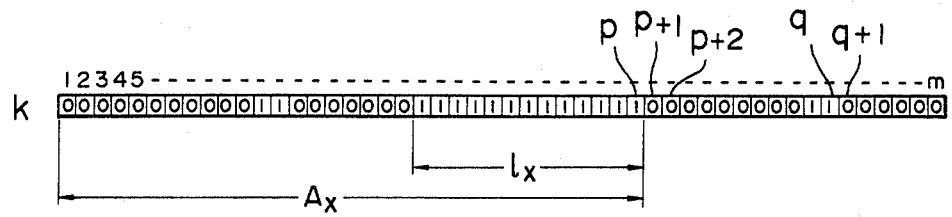

The video memory IPM stores "1" for the white portion of the image shown in FIG. 17 and "0" for the black portion. The data preparing circuit LC has an inverter NOT to invert the signal read out of the video memory IMP. Thus, the white portion of the image is read in as "0" and the black portion is read in as "1". FIG. 19b shows the output of the inverter NOT corresponding to FIG. 19a.

Figure 20:
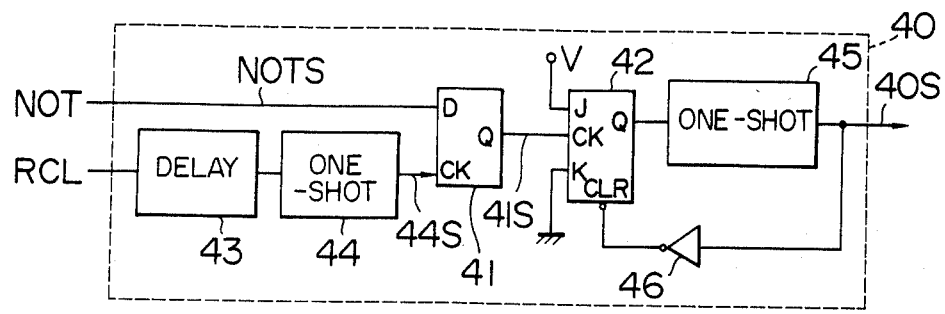
FIG. 20 shows a block diagram of a fall detector.
Figure 21:
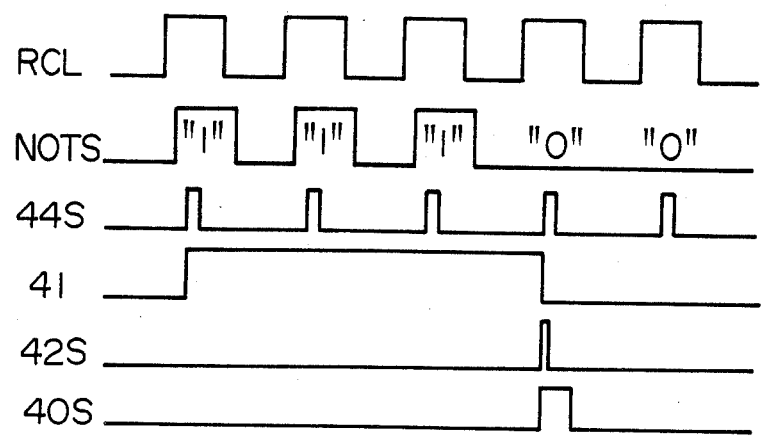
FIG. 21 shows a time chart for waveforms at various points in FIG. 20.

The fall detection circuit 40 detects when the image changes from black to white, that is, from "0" to "1" in FIG. 19a to produce an output. The signal from the video memory IPM is supplied to the circuit 40 through an inverter NOT so that the circuit 40 actually detects the fall from "1" to "0" (FIG. 19b). FIG. 20 shows an example of the fall detection circuit 40. It comprises a D-type flip-flop 41 and a JK flip-flop 42. The read clock pulse RCL and the output from the inverter NOT are supplied to the circuit 40 so that it detects the fall point from those signals and produces a fall signal 40S. The output of the inverter NOT is supplied to an input terminal D of the D-type flip-flop 41. The inverted contents of the respective lines of the video memory IMP are sequentially supplied to the terminal D by the read circuit R. Referring to FIG. 19a, the inversions of the signals shown therein, that is, the signals "1" for the signals "0" and the signals "0" for the signals "1" are sequentially supplied. The read clock pulse RCL is supplied to a clock terminal CK of the D-type flip-flop 41 through a delay circuit 43 and a one-shot pulse generator 44. When the D-type flip-flop 41 receives the clock signal at its clock terminal CK, it temporarily stores a signal which is currently present at its input terminal D and supplies it from an output terminal Q. The video memory IPM needs a certain time from the addressing to the readout of the addressed memory content. Accordingly, even if the read clock pulse RCL is directly applied to the clock terminal CK, the memory content of the address to be read by that read clock RCL cannot be stored in the D-type flip-flop 41. Accordingly, the read clock pulse RCL is delayed by the delay circuit 43 by that time period and the rise of the delayed output is detected by the one-shot pulse generator 14 to produce a clock signal. The output of the D-type flip-flop 41 is supplied to a clock terminal CK of the JK flip-flop 42 having its input terminal J connected to a power supply V or "1" and its input terminal K connected to ground or "0". The output of the circuit 42 is produced as an output of the fall detection circuit 40 through a one-shot pulse generator 45. The output of the one-shot pulse generator 45 is also supplied to a clear terminal CLR of the JK flip-flop 42 through an inverter 46 to clear the flip-flop 42. FIG. 21 shows a time chart for the circuit of FIG. 20, in which RCL is the read clock pulse RCL, NOTS is the output of the inverter NOT, 44S is the output of the one-shot pulse generator, 41S is the output of the D-type flip-flop 41, 42S is the output of the JK flip-flop 42, and 40S is the output of the one-shot pulse generator 45, which is the output of the fall detection circuit 40, that is, the fall signal. As seen from FIG. 21, the read clock pulse RCL is generated at a constant period, the stored contents of the video memory IPM are sequentially read and the fall signal 40S is produced when the read signal changes from "1" to "0".

The joint detection circuit LX comprises counters 51 and 52, a data selector 53, a comparator 54, AND gates 55, 56 and 57 and flip-flops 58 and 59. The counters 51 and 52 count the numbers of pulse signals applied to their count input terminals CK and supply the counts as output data. The data selector 53 receives the data from the counters 51 and 52 and selects one of them in accordance with a signal to a select terminal SLT. If a "1" signal is supplied to the select terminal SLT, it selects the data applied to an input terminal A, that is, the count of the counter 51, and if a "0" signal is supplied to the select terminal SLT, it selects the data applied to an input terminal B, that is, the count of the counter 52. The comparator 54 compares the data applied to the input terminal A, that is, the count of the counter 51 with the data applied to the input terminal B, that is, the count of the counter 52, and if they are equal, it produces a "1" signal from an output terminal A=B, if the data at the input terminal A is larger, it produces the "1" signal from an output terminal A>B, and if the data at the input terminal B is larger, it produces the "1" output from an output terminal A<B. The outputs from the output terminals A=B, A>B and A<B are supplied to the corresponding AND gates 55, 56 and 57 which also receive the fall signal 40S from the fall detection circuit 40. Accordingly, the AND gates 55, 56 and 57 each produces a "1" signal if the "1" signal from the comparator 54 is supplied thereto when the fall signal 40S is applied. The output of the AND gate 56 is supplied to a set terminal S of the flip-flop 58 and the output of the AND gate 57 is supplied to a reset terminal R. An output from an output terminal Q of the flip-flop 58 is supplied to the select terminal SLT of the comparator 53. Thus, if the count of the counter 51 is larger than the count of the counter 52 when the fall signal 40S is supplied, the flip-flop 58 is set and the "1" signal is applied to the select terminal SLT of the data selector 53 so that the data selector 53 produces the count of the counter 51 applied to the input terminal A. On the other hand, if the count of the counter 52 is larger than the count of the counter 51 when the fall signal 40S is supplied, the flip-flop 58 is reset and the "0" signal is applied to the select terminal SLT of the data selector 53 so that the data selector 53 produces the count of the counter 52 applied to the input terminal B. When the counts of the counters 51 and 52 are equal, the output of the flip-flop 58 does not change and the data selector 53 produces the count of one of the counters 51 and 52 which was formerly selected.

The flip-flop 59 receives the outputs of the AND gates 55 and 56 at its set terminal S through an OR gate 60 and receives the output of the AND gate 57 at its reset terminal R. An output from an output terminal Q is supplied to a one-shot pulse generator 61 through an AND gate AND2, and a pulse signal produced by the circuit 61 is applied to a clear terminal CLR of the counter 52 through an OR gate 62. An output from an inverting output terminal $\overline{Q}$ of the flip-flop 59 is supplied to a one-shot pulse generator 63 through an AND gate AND1, and a pulse signal produced by the circuit 63 is applied to a clear terminal CLR of the counter 51 through an OR gate 64. The fall signal 40S is supplied to the AND gates AND1 and AND2. The output of the inverter NOT is supplied to the count input terminals CK of the counters 51 and 52 through AND gates 65 and 66, respectively. The output from the output terminal Q of the flip-flop 59 is supplied to the AND gate 66 through a delay circuit 67, and the output from the output terminal $\overline{Q}$ is supplied to the AND gate 65 through a delay circuit 68. Thus, when one or both of the AND gates 55 and 56 produces the outputs, that is, if the count of the counter 51 is larger than or equal to the count of the counter 52, the flip-flop 59 is set and the counter 52 is cleared by the output of the output terminal Q. On the other hand, if the count of the counter 52 is larger than the count of the counter 51, the flip-flop 59 is reset by the output of the AND gate 57 and the counter 51 is cleared by the output of the output terminal $\overline{Q}$. Thus, the maximum count in the past is stored in one of the counters 51 and 52 and the smaller count in the other counter is cleared. As the flip-flop 59 is set, the AND gate 66 is opened and the AND gate 65 is closed after the delay time by the delay circuits 67 and 68. Conversely, when the flip-flop 59 is reset, the AND gate 66 is closed and the AND gate 65 is opened after the delay time by the delay circuits 67 and 68. The delay circuits 67 and 68 are provided to prevent a signal from being supplied to the counter 51 or 52 while it is being cleared. With such an arrangement, one of the AND gates 65 and 66 is open at a certain time point and the corresponding one of the counters 51 and 52 counts the signal from the inverter NOT. The content of one of the counters 51 and 52 which has smaller count by the comparison when the fall signal 40S is produced is cleared and the corresponding one of the AND gates 65 and 66 is substantially simultaneously opened so that the cleared counter 51 or 52 next starts to count.

Figure 22:
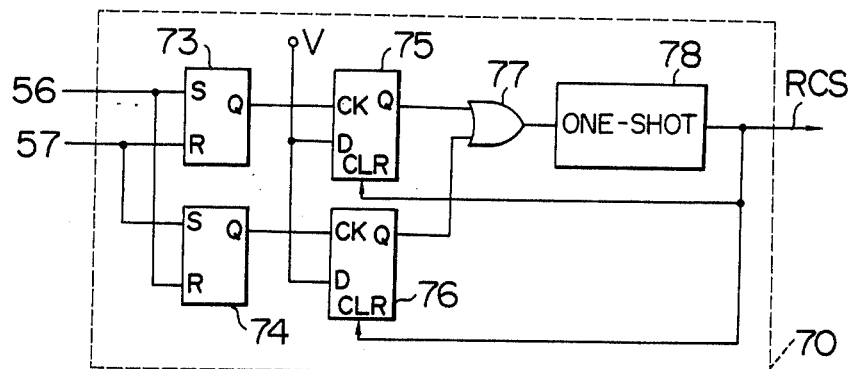
FIG. 22 shows a block diagram of a register control circuit.

The joint end detection circuit AX comprises a counter 71, a register 72 and a register control circuit 70. The counter 71 counts the number of input pulses to a count input terminal CK thereof and supplies the content thereof to the register 72. The register 72 temporarily stores the input from the counter 71 at a fall of a signal supplied to a load terminal L and supplies the stored content. The signal to the load terminal L of the register 72 falls when the compare output of the comparator 54 shifts from the output terminal A>B to the output terminal A<B or from the output terminal A<B to the output terminal A>B. It also falls when the compare output shifts from the output terminal A=B at the initial state to the output terminal A>B. This is effected by the register control circuit 70. FIG. 22 shows an example of the register control circuit 70. It attains the function by receiving the output of the AND gate 56 corresponding to the output terminal A>B of the comparator 54 and the output of the AND gate 57 corresponding to the output terminal A<B. To this end, it comprises SR flip-flops 73 and 74, D-type flip-flops 75 and 76, an AND gate 77 and a one-shot pulse generator 78. The output from the AND gate 56 is supplied to a set terminal S of the flip-flop 73 and a reset terminal R of the flip-flop 74. The output from the AND gate 57 is supplied to a reset terminal R of the flip-flop 73 and a set terminal S of the flip-flop 74. Input terminals D of the flip-flops 75 and 76 are connected to a power supply V. That is, a "1" signal is always supplied to those terminals D. The output of the flip-flop 73 is supplied to a clock terminal CK of the flip-flop 75 and the output of the flip-flop 74 is supplied to a clock terminal CK of the flip-flop 76. The outputs of the flip-flops 75 and 76 are supplied to the OR gate 77, the output of the OR gate 77 is supplied to the one-shot pulse generator 78, and the output of the one-shot pulse generator 78 is supplied to the load terminal L of the register 72 as the register control signal RCS. The output of the one-shot pulse generator 78 is also supplied to clear terminals CLR of the flip-flops 75 and 76. Thus, when one of the AND gates 56 and 57 produces the signal, one of the flip-flops 73 and 74 which receives the signal at its set terminal S is set and the other is reset. As a result, the one flip-flop 75 or 76 produces the "1" signal and the output of the OR gate 77 causes the one-shot pulse generator 75 to produce the register control signal RCS. The flip-flops 75 and 76 are cleared to the initial state by the signal RCS.

Figure 23:
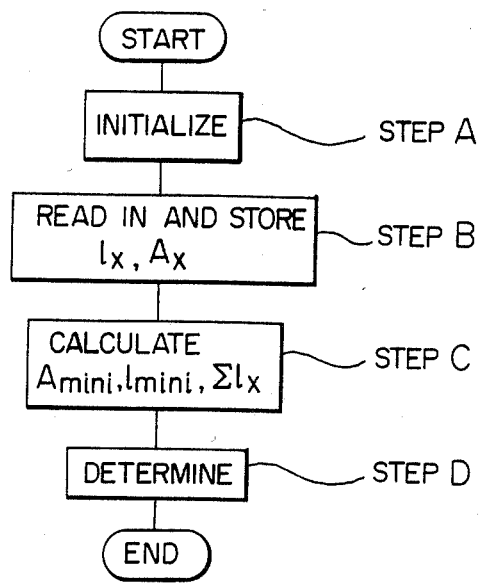
FIG. 23 shows a flow chart for a control sequence of an arithmetic and processing unit.
Figure 24:
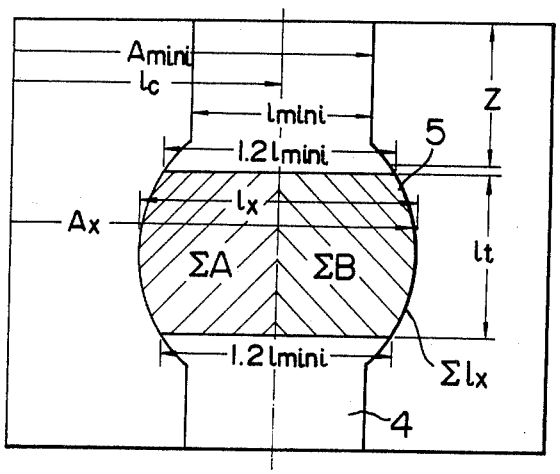
FIG. 24 shows a chart for explaining the operation of the arithmetic and processing unit.

The processor CPU reads in various data necessary for the decision from the video memory IPM through the read circuit R and the data preparing circuit LC to determine the condition of the joint 5. In the illustrated embodiment, it comprises a microcomputer. The microcomputer executes processing and arithmetic operations in accordance with a program stored in a program memory. FIG. 23 shows a flow chart of the program. The processor CPU first initializes the conditions in a step A. For example, a data memory for temporarily storing the data supplied from the data preparing circuit LC is cleared and a data memory for storing an interim result of the operation is cleared. In a step B, the joint data lx and the joint end data Ax for each line of the video memory IPM shown in FIG. 19 are read through the read circuit R and the data preparing circuit LC and they are stored in the data memory. In a step C, the data necessary to determine the condition of the joint 5 are calculated based on the joint data lx and the joint end data Ax for each line stored in the data memory. In the following description, the data are defined as follows. Referring to FIG. 24, the joint data lx represents the length of the joint 5 or the number of bits in any line of FIG. 17, and the joint end data Ax represents the length or the number of bits from the left end of the line to the right end of the joint 5. Amini represents a minimum of the joint end data Ax and lmini represents a minimum of the joint data lx. The lmini eventually corresponds to the diameter of the lead wire 4. The lc represents the length or the number of bits from the left end of the line to the center C of the lead wire 4. The lt represents the length or the number of bits of a portion of the joint 5 having a length longer than 1.2 lmini. The ΣA represents an area or total number of bits of the joint 5 within the range of lt on the left side of the center line of the lead wire 4, the ΣB represents a similar area or total number of bits on the right side, and the Σlx represents an area or total number of bits of the joint 5 within the range of lt. As seen from FIG. 24, the Σlx is a sum of the ΣA and the ΣB. From those data, the Amini, lmini and Σlx are calculated in the step C. Based on those data, the condition of the joint 5 is determined in a step D.

The processor CPU produces an initial clearing signal ICL and a clock generation instruction signal CLI at appropriate timing and receives the signal from the overflow terminal OFL of the one-line clock generator 30 and the joint data lx and the joint end data Ax from the data preparing circuit LC at appropriate timing to execute the operation and processing. The initial clearing signal ICL from the processor CPU is supplied to the OR gates 62 and 64 of the data preparing circuit LC and the clear terminal CLR of the counter 71.

Figure 25:
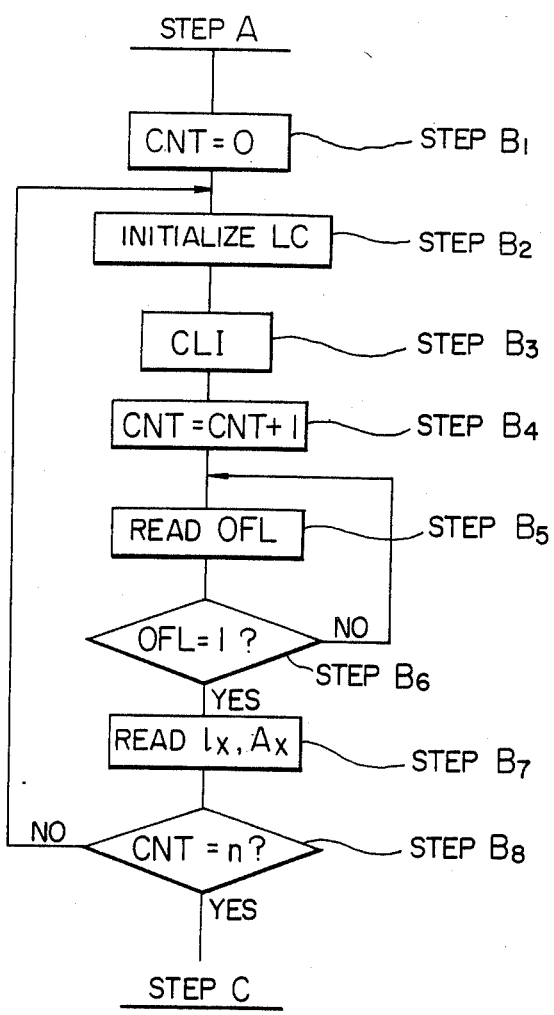
FIGS. 25, 26 and 27 show flow charts for the processing of FIG. 23.
Figure 26:
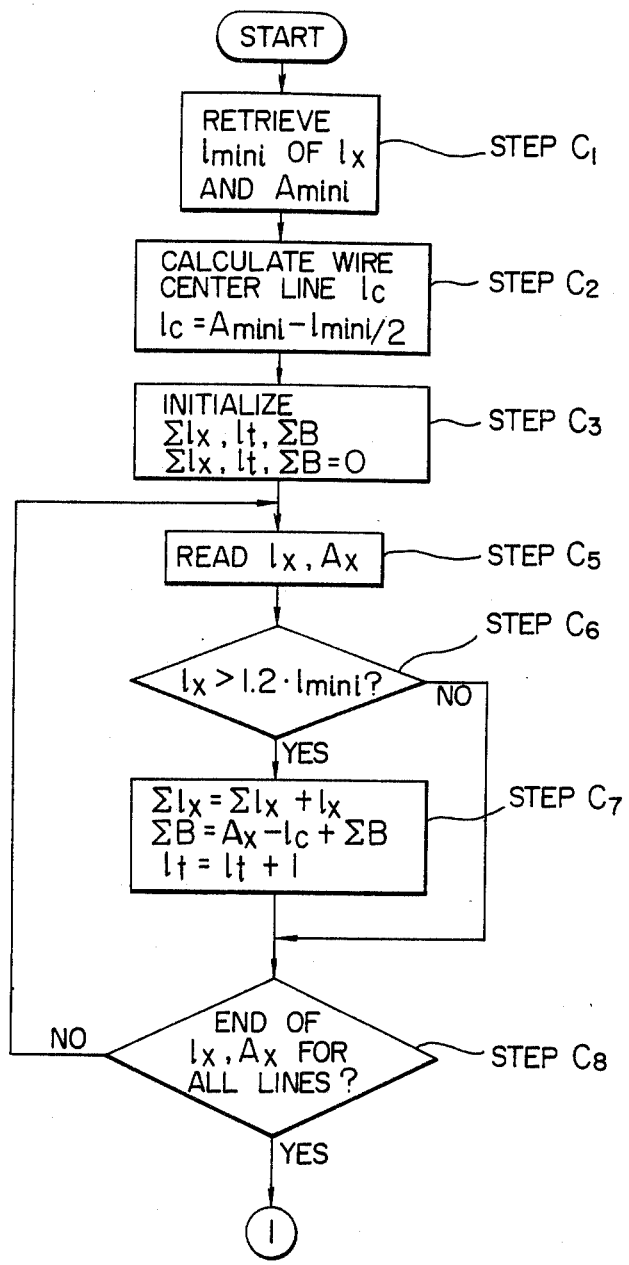
Figure 27:
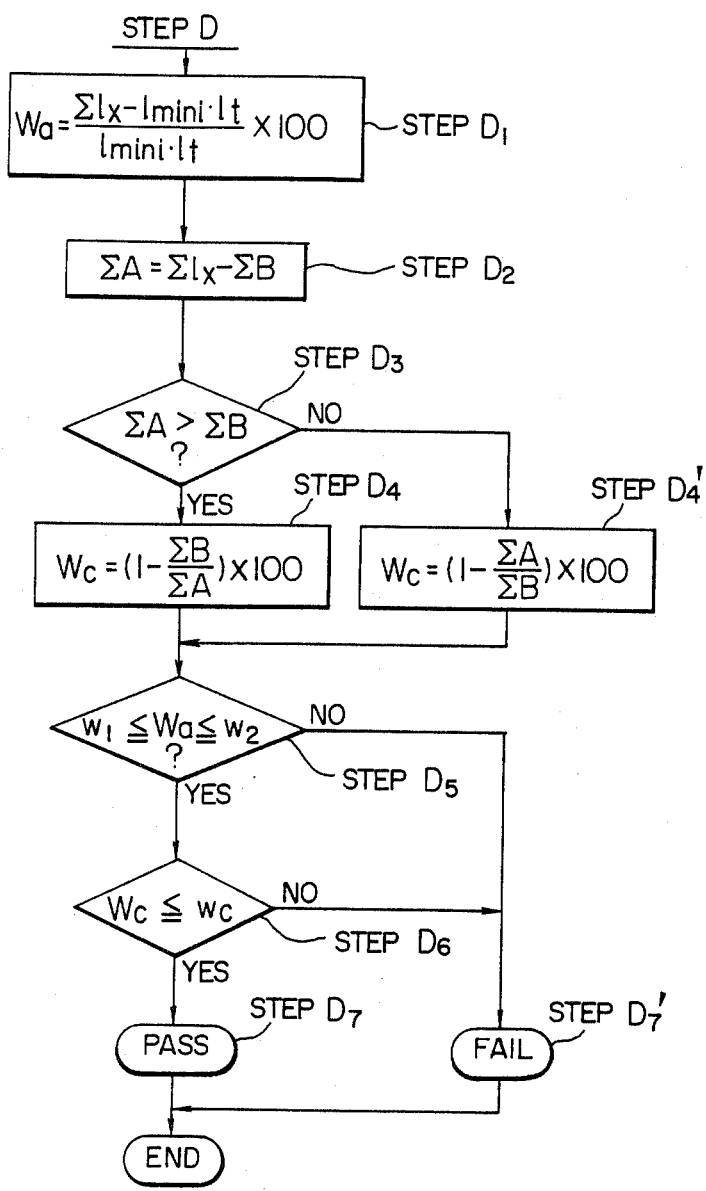

FIGS. 25, 26 and 27 show flow charts of details of the steps B, C and D of FIG. 23. An overall operation is now explained with reference to those drawings. In the step B shown in FIG. 25, a counter CNT is reset to zero in a step B1. The counter CNT is a software counter which is assigned with predetermined addresses on the data memory. The counter CNT is a line counter which counts each line of the video memory IMP. In a step B2, the data preparing circuit LC is initialized. The initial clearing signal ICL is supplied to the OR gates 62 and 64 of the circuit LC and the clear terminal CLR of the counter 71. As a result, the counters 51, 52 and 71 are cleared. In a step B3, the clock generation instruction signal CLI is supplied to the read circuit R, and in a step B4 the counter CNT is incremented by one. When the clock generation instruction signal CLI is supplied to the read circuit R in the step B3, the read circuit R sequentially reads out the content stored in the first line of the video memory IPM. In a step B5, the output of the overflow terminal OFL of the counter 35 is read, and in a step 6 it is checked if the output of the overflow terminal OFL is "1", that is, if the read circuit R has completed to generate the clock pulses for one line of the video memory IPM. The steps B5 and B6 are repeated until the overflow signal is produced from the overflow terminal OFL. If the overflow signal is detected in the step B6, the joint data lx and the joint end data Ax are read from the data preparing circuit LC in a step B7 and they are stored in the data memory. In a step B8, it is checked if the content of the counter CNT is n, that is, if the video memory IMP has been scanned to the last line and the steps B2 to B8 are repeated until the condition is met. When the video memory IPM has been scanned to the last line and the content of the counter CNT reaches n, the process goes to the step C.

In the step B3, when the clock generation instruction signal CLI is supplied to the read circuit R, the read circuit R sequentially reads out one line of the video memory IPM from the left end and supplies it to the data preparing circuit LC. The flip-flop 59 of the circuit LC is either set or reset when the power is turned on. Let us assume that the flip-flop 59 is in the set state and a sequence of data shown in FIG. 19 are read from the video memory IPM sequentially from the left end in accordance with the clock from the one-line clock generator 30. Since the flip-flop 59 is in the set state, the AND gate 65 is opened and the AND gate 66 is closed. Accordingly, the counter 51 counts the number of the "1" signals supplied from the inverter NOT (see FIG. 19b). The counter 71 sequentially counts the read clock pulses RCL from the one-line clock generator 30. At the transition from the fifth bit to the sixth bit, the data falls from "1" to "0". The fall detection circuit 40 detect it and produces the fall signal 40S. At this time, the count of the counter 51 is "2", the count of the counter 52 is "0" and the count of the counter 71 is "5". Accordingly, the AND gate 56 produces the signal and the selector 53 produces the count "2" of the counter 51. The flip-flop 59 is set so that the AND gate 65 is closed and the AND gate 66 is closed. The register control circuit 73 produces the register control signal RCS and the count "5" of the counter 71 is set in the register control circuit 73. Since the video memory IPM continuously supplies the signal, the following "1" is counted by the counter 52. When the data falls from "1" to "0" at the p-th bit, the fall detection circuit 40 detects it and produces the fall signal 40S. At this time, the count of the counter 51 is "2", the count of the counter 52 is "lx" and the count of the counter 71 is "Ax". As the fall signal 40S is produced, the flip-flop 58 is reset because the count "lx" of the counter 52 is larger than the count "2" of the counter 51, and the selector 53 selects the count "lx" of the counter 52. The flip-flop 59 is reset so that the AND gate 66 is closed and the AND gate 65 is opened and the counter 51 is cleared. The register control signal RCS is produced and the count "AX" of the counter 71 is set in the register 72. Subsequently, the counter 51 counts the number of the "1" signals from the inverter NOT. When the data falls from "1" to "0" at the g-th bit, the fall detection circuit 40 detects it and produces the fall signal 40S. At this time, the count of the counter 51 is "3", the count of the counter 52 is "lx" and the count of the counter 71 is "g". As the fall signal 40S is generated, the flip-flop 58 is again reset because the count "lx" of the counter 52 is larger than the count "3" of the counter 51 and the selector 53 again selects the count "lx" of the counter 52. The flip-flop 59 is again reset so that the AND gate 66 is closed, the AND gate 65 is opened and the counter 51 is cleared. At this time, the register control circuit 73 does not produces the register control signal RCS and the register 72 maintains the count "Ax". One line of data are read by the read circuit R until the m-th bit is read and the "lx" produced by the selector 53 and the "Ax" produced by the register 72 do not change. Accordingly, in the step B7, the processor CPU can correctly read the joint data lx and the joint end data Ax.

Since the data preparing circuit LC is constructed as shown in FIG. 11, even if the image from the TV camera 20 includes a black pattern or defect of the semiconductor integrated circuit 2 other than the joint 5, it is not counted and only the joint 5 is counted. This is due to the fact that the width of the joint 5 is larger than that of the other pattern or defect.

The steps B2 to B8 are repeated so that the joint data lx and the joint end data Ax for n lines of the video memory IPM are stored in the data memory of the processor CPU.

After the above processing, the processor CPU calculates various data necessary to determine the condition of the joint 5 based on the contents stored in the data memory. Referring to FIG. 26, in a step C1, lmini and Amini are retrieved. The lx of the respective lines are sequentially read from the data memory, compared to each other and the smallest one of them is set as lmini, and the corresponding Ax is set as Amini, and they are stored in the data memory. In a step C2, a length lc to the center C of the lead wire 4 is calculated. This is effected by subtracting $\frac{1}{2}$ lmini from Amini as seen from FIG. 24. In a step C3, the addresses of the data memory at which the joint area Σlx, the effective joint length lt and the area ΣB are to be stored are cleared in preparation for the execution of the subsequent steps. In a step C5, lx and Ax for each of the lines are read. In a step C6, it is checked if lx is larger than 1.2 lmini or not, and if it is larger, the value of lx is set as Σlx in a step C7. Ax−lc is added to ΣB and one is added to the joint length lt. If lx is not larger than 1.2 lmini in the step C6, the value of this line is neglected and the process goes to a step C8. In the step C8, it is checked if the steps C5, C6 and C7 have been executed for the respective lines, and if not, the steps C5, C6 and C7 are executed for the next line. The steps C5, C6 and C7 are repeated for each line, that is, n times as seen from FIG. 17. If the end of the processing for the respective lines is determined in the step C8, the process goes to the step D. At this time, the number of bits corresponding to the joint lx, that is, the value stored in the data memory is stored at the address Σlx for the joint area. The corresponding numbers of bits are also stored at the addresses lt and ΣB.

Figure 5:
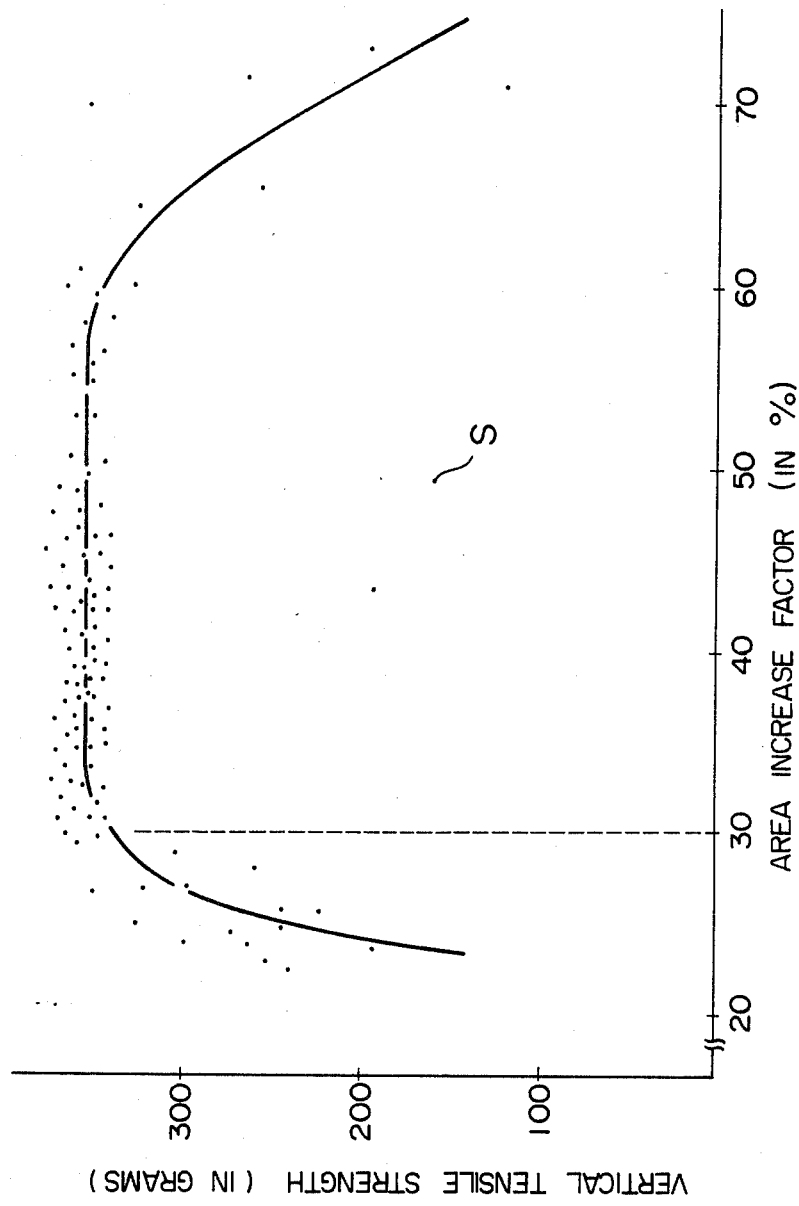
FIG. 5 shows a chart for explaining the present invention.
Figure 6:
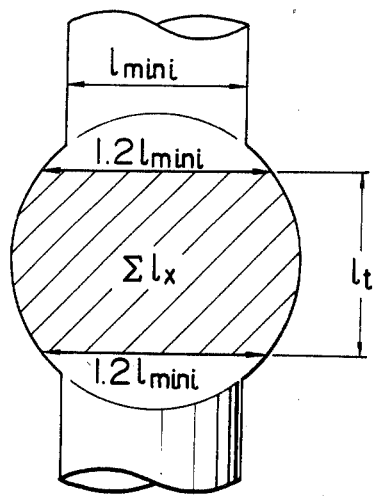
FIGS. 6, 7, 8 and 9 show plan views of joints for explaining the present invention.
Figure 7:
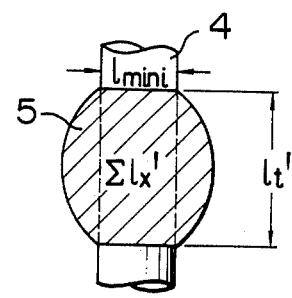
Figure 8:
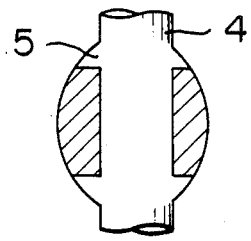
Figure 9:
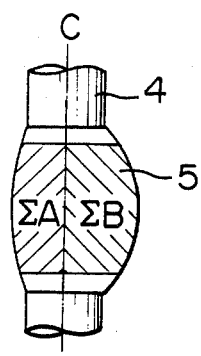
Figure 10:
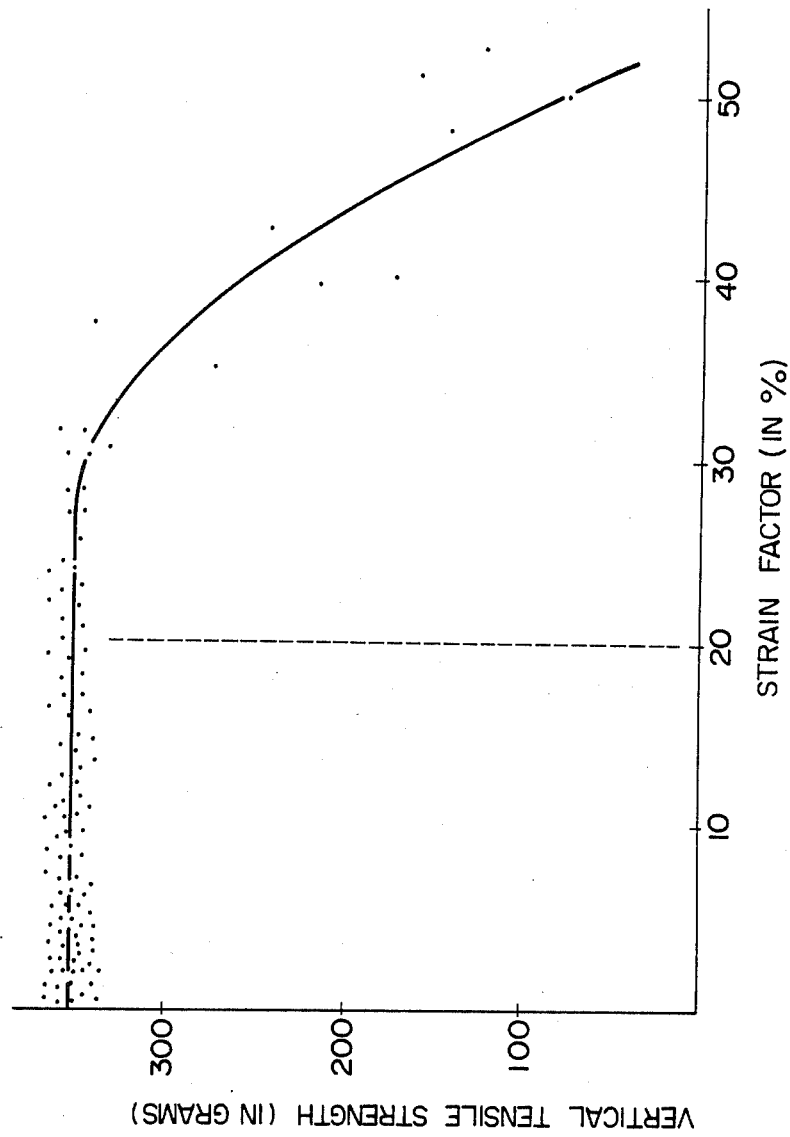
FIG. 10 shows a chart for explaining the present invention.

In the step D, the decision is made based on the calculated data. Referring to FIG. 27, the area increase factor Wa is calculated in a step D1, in accordance with the formula (1). A result thereof is stored at a predetermined address Wa of the data memory. In a step D2, ΣA is calculated based on Σlx and ΣB calculated in the step C and a result thereof is stored in the data memory. Based on those results, the strain factor Wc is calculated. In a step D3, ΣA and ΣB are compared, and depending on the compare result, the strain factor Wc is calculated in either a step D4 or a step D4', and a result thereof is stored in the data memory. Then the decision is made. In a step D5, the area increase factor Wa stored in the data memory is read and it is compared with a minimum allowable area increase factor W1 and a maximum allowable area increase factor W2. If the area increase factor Wa is within the range, the process goes to a step D6, and if it is not within the range, the process goes to a step D7' where a fail decision is made. The minimum and maximum allowable area increase factors W1 and W2 correspond to 30% and 50%, respectively, in FIG. 5. In a step D6, the strain factor Wc is checked. The strain factor Wc stored in the data memory is read and it is compared with a maximum allowable strain factor wc. If the strain factor Wc is not larger than wc, the pass decision is made in a step D7, and if it is larger than wc, the fail decision is made in the step D7'. The maximum allowable strain factor wc corresponds to 20% in FIG. 10. In the steps D7 and D7', the processor CPU produces signals representing the decision result. For example, for the signal from the step D7', an alarm is issued or the failed product is rejected from a line. For the signal from the step D7, the passed product is fed to the next stage and the test for the next product is effected. In this manner, a series of tests is completed.

In the above embodiment, the read circuit R, the video memory IPM and the data preparing circuit LC are arranged around the processor CPU to increase a test speed. However, those peripheral circuits may be omitted if a specification of the test apparatus allows it. Thus, the signal from the TV camera 20 may be digitized by the digitizing circuit BC and the processor CPU may directly read in the digitized signal to execute the processing. The video memory IPM may be added thereto so that the processing is executed by the cooperation of the video memory IPM and the processor CPU.

While the location of the installation of the TV camera 20 is not specifically described, it may be any position to permit imaging of the joint 5. For example, it may be mounted on an arm of the bonding apparatus. In the illustrated embodiment, the TV camera 20 is arranged relative to the joint 5 such that the joint 5 is parallel with the edge of the image plane, that is, the center line of the lead wire 4 is parallel to the edge of the image. However, the present invention is not limited thereto. Even if the joint 5 is inclined relative to the edge of the image plane, it can be detected or even the inclination can be corrected.

In the above embodiment, the joint joined by the ultrasonic wave type wire bonding apparatus is the subject of the test. However, the present invention is not limited thereto and it is also applicable to the test of the joint formed by a wire bonding apparatus of a thermal press type as represented by a ball method or a steck method. The present invention is also not limited to the test of the joint formed by the ultrasonic wave bonding or diffusion bonding as represented by the thermal press bonding. The present invention is applicable to the test of the joint formed by welding such as fusing or pressing, or other bonding method. In the illustrated embodiment, the joint between the lead wire 4 and the semiconductor integrated circuit element or the post 3 is described. However, the present invention is not limited to those elements and the number of elements is not restrictive.

Figure 28:
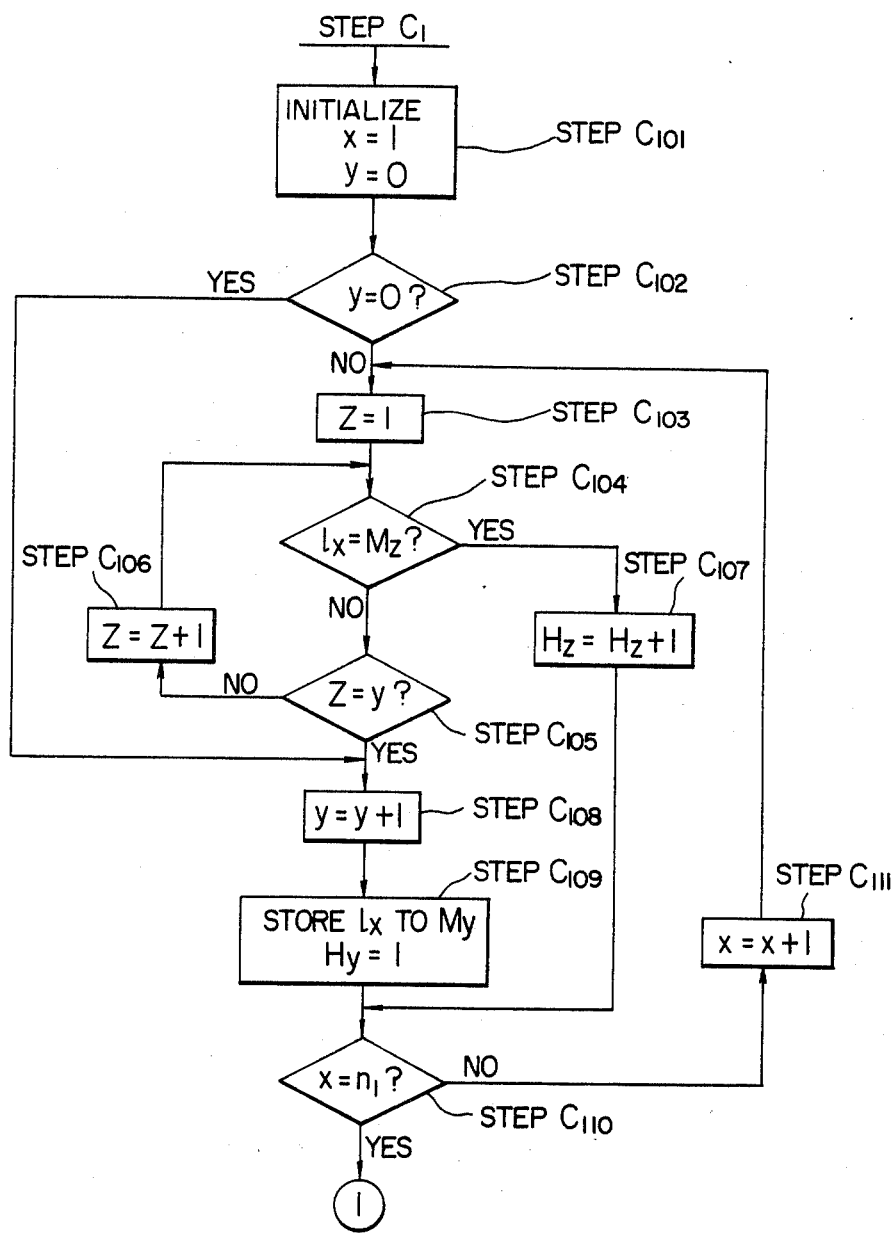
FIGS. 28, 29 and 30 show flow charts for other processing.
Figure 29:
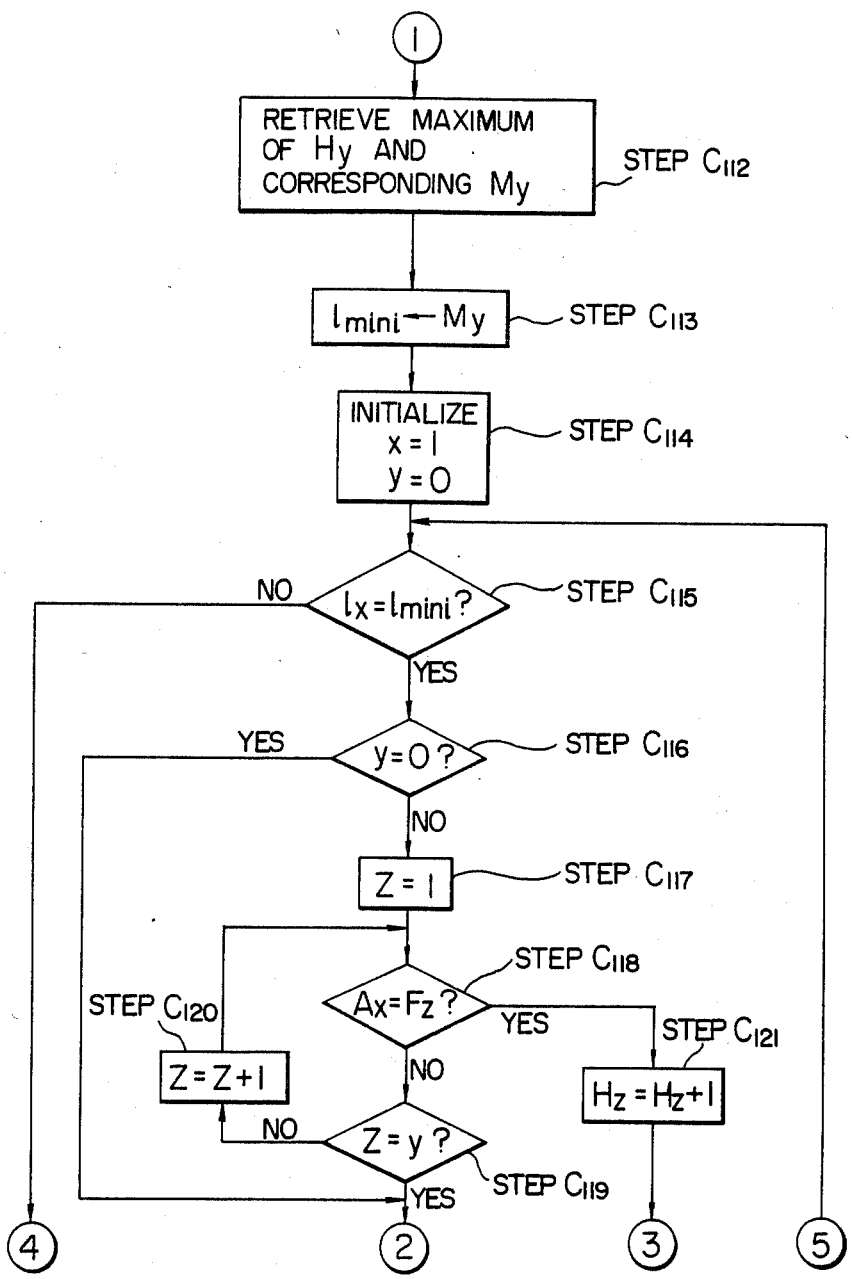
Figure 30:
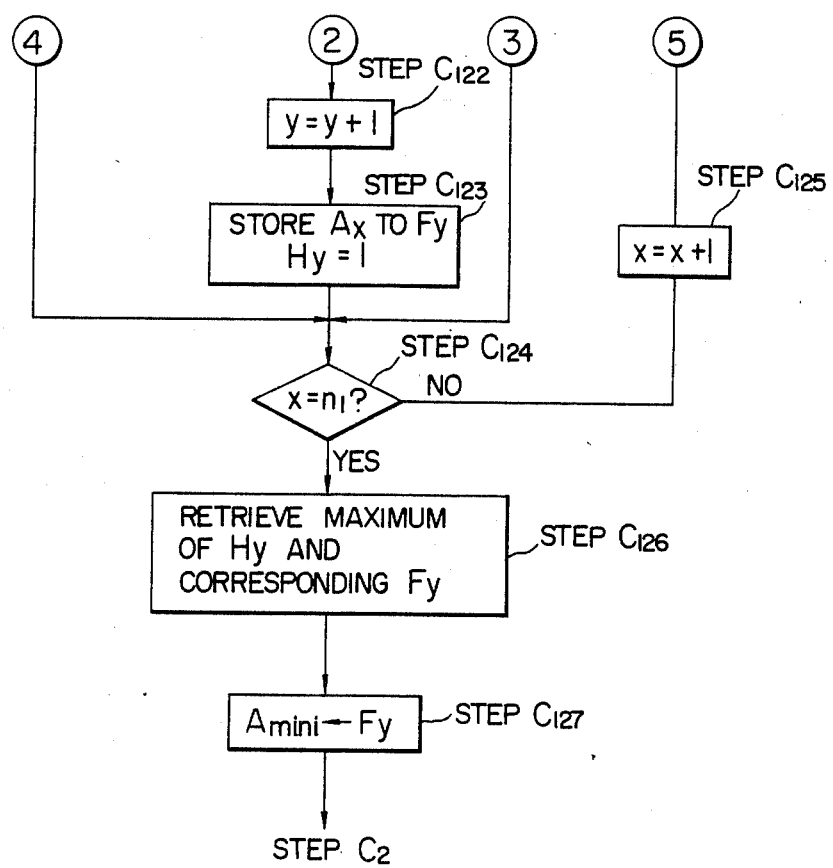
Figure 31:
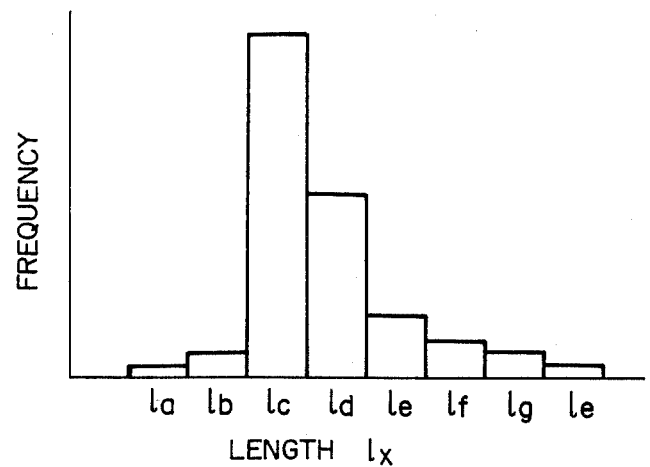
FIGS. 31 and 32 show charts for explaining FIGS. 28, 29 and 30.
Figure 32:
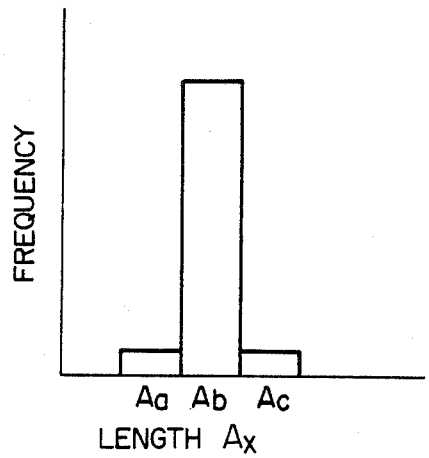

In the illustrated embodiment, as seen from the step C1 of FIG. 26 and the related description, the width of the lead wire lmini and Amini are determined by sequentially reading lx of the respective lines from the data memory, comparing them to determine the minimum one of them as lmini and the corresponding one of Ax as Amini. Alternatively, they may be determined in manners shown in FIGS. 28-30. In those figures, the circled numerals indicate the interconnection. Width data lx for the respective lines in a region Z which includes the lead wire 4 as shown in FIG. 24 are sequentially read out. A histogram as shown in FIG. 31 is prepared and a highest frequency width data lc is set as the width lmini of the lead wire 4. For Ax corresponding to the width data lc or lx representing lmini, a histogram similar to that of FIG. 31 is prepared as shown in FIG. 32, and a highest frequency data Ab is set as Amini. The data lmini and Amini thus determined are stored in the data memory. The flow charts are now explained.

A variable x is a counter for sequentially reading lx from the first line to a specified line $n_1$, a variable y is a counter for counting the number of representative values of lx and a variable z is a counter for sequentially comparing a newly read lx with the representative value. The counters x, y and z are software counters having predetermined addresses on the data memory. In a step $C_{101}$, the counters x and y are initialized. The counter x is set to "1" to permit reading from the first line, and the counter y is set to "0" because no representative value has been received yet. In a step $C_{102}$, the content of the counter y is compared with zero to check if the number of the representative value is "0". Since the content of the counter y is "0" at first (for the first line), the process goes to a step $C_{108}$. In the step $C_{108}$, the content of the counter y is incremented by one. In a step $C_{109}$, the lx for the first line is stored at an address My and a counter Hy for counting the frequency is initialized. In a step $C_{110}$, the content of the counter x is compared with $n_1$ to check if lx for all lines have been read. If not, the counter x is incremented by one in a step $C_{111}$ and the process goes to a step $C_{103}$. In the step $C_{103}$, the counter z is initialized. In a step $C_{104}$, a newly read lx is compared with Mz to check if it is equal to one of the stored representative values. If it is equal, the process goes to a step $C_{107}$ and a counter Hz for counting the frequency of the representative value is incremented by one. Then the process goes to a step $C_{110}$. If lx is not equal to Mz in the step $C_{104}$, the process goes to a step $C_{105}$ and the content of the counter z is compared with the content of the counter y to check if the comparison has been made with all of the stored representative values. If not, the process goes to a step $C_{106}$ and the counter z is incremented by one to read the next representative value. When all of the representative values are compared, the process goes to a step $C_{108}$ and the counter y is incremented by one. In a step $C_{109}$, lx is stored at My as the representative value and the counter Hy is initialized. In the step $C_{110}$, if all lines have been read, they result in the histogram shown in FIG. 31. Then, the process goes to a step $C_{112}$. In the step $C_{112}$, a maximum one of the frequencies Hy for the representative values is retrieved, and the corresponding representative value is retrieved from My. In a step $C_{113}$, the My is set as lmini.

The Amini is next determined. This process is substantially similar to that for the lmini except that the Ax is determined by the condition that the lx of the corresponding line is equal to lmini. This is effected by comparing lx with lmini in a step $C_{115}$. The steps for the Amini correspond to the steps of lmini in the following manner: $C_{101}$ and $C_{114}$, $C_{102}$ and $C_{116}$, $C_{103}$ and $C_{117}$, $C_{104}$ and $C_{118}$, $C_{105}$ and $C_{119}$, $C_{106}$ and $C_{120}$, $C_{107}$ and $C_{121}$, $C_{108}$ and $C_{122}$, $C_{109}$ and $C_{123}$, $C_{110}$ and $C_{124}$, $C_{111}$ and $C_{125}$, $C_{112}$ and $C_{126}$, and $C_{113}$ and $C_{127}$. By detecting the lmini and Amini in this manner, the width of the joint to be tested can be more exactly measured and the accuracy of the test of the joint can be further enhanced.

We claim:
1. A method for testing the strength of a joint comprising the steps of:
measuring a deformed area of a joint which is formed by members joined by joining means;
comparing said deformed area with a reference area predetermined for strength test of the joint; and
making a test decision of the strength of the joint on the basis of the result of the comparison.

2. A method for testing a joint according to claim 1 wherein said joint is formed by joining a members by welding.

3. A method for testing a joint according to claim 1 wherein said joint is formed by joining a lead wire to a member by a wire bonding apparatus.

4. A method for testing a joint according to claim 1 wherein said reference area includes a maximum allowable area and a mininum allowable area and the comparison is made by checking if the deformed area of said joint is within a range defined by said maximum and minimum allowable areas.

5. A method for testing a joint according to claim 1 wherein the comparison is made based on a ratio of the deformed area to the reference area.

6. A method for testing a joint according to claim 5 wherein said reference area is an area of said joint before joining.

7. A method for testing a joint according to claim 5 wherein said two halves of said joint are divided by a center line of said joint before joining.

8. A method for testing a joint according to claim 1 further comprising the steps of:
dividing said deformed area into two halves; and
comparing one of areas of the two halves with the other;
whereby the test decision is made on the basis of the results of the comparison between the deformed area and the reference area.

9. A method for testing a joint according to claim 1 wherein the measurement of said deformed area is made by imaging said joint after joining on an image plane, extracting the deformed area of said joint from the image and calculating the extracted area.

10. A method for testing a joint according to claim 9 wherein the image is exposed on the image plane having a plurality of picture cells and the deformed area of said joint is calculated by the number of picture cells exposed.

11. A method for testing the strength a joint of a first member joined by joining means, comprising:
(a) a first step of measuring a deformed area of said joint;
(b) a second step of calculating a ratio of said joint area measured in said first step to a reference area predetermined for strength test of the joint; and
(c) a third step of checking if said ratio calculated in said second step is within a predetermined allowable area ratio range, whereby said joint is tested.

12. A method for testing a joint of a first member and a second member joined by a joining means comprising:
(a) a first step of measuring a deformed area of said joint;
(b) a second step of comparing said deformed joint area measured in said first step with a predetermined minimum allowable area and a predetermined maximum allowable area; and
(c) a third step of making a pass decision when a compare result in said second step shows that said deformed joint area is no larger than said minimum allowable area and no smaller than said maximum allowable area and making a fail decision otherwise.

13. An apparatus for testing a joint comprising:
imaging means for imaging a joint which is formed by members joined by joining means on an image plane and producing an electric signal representative of the image on said image plane; and
processing means adapted to receive said electric signal from said imaging means for extracting a deformed area of said joint from said electric signal and comparing said deformed area with a reference area predetermined for a strength test of said joint as a test decision of the strength of said joint.

14. An apparatus for testing a joint according to claim 13 wherein said joint is formed by members joined by welding.

15. An apparatus for testing a joint according to claim 13 wherein said joint is formed by joining a lead wire to a member by a wire bonding apparatus.

16. An apparatus for testing a joint accoridng to claim 13 wherein said imaging means includes a solid state imaging element having a plurality of picture cells.

17. An apparatus for testing a joint according to claim 16 wherein said processing means includes digitizing means for digitizing the image signal from said imaging means for each picture cell.

18. An apparatus for testing a joint according to claim 17 wherein said processing means includes video memory means for temporarily storing the output from said digitizing means for each picture cell to digitally store the image formed on the image plane of said imaging means.

19. An apparatus for testing a joint according to claim 18 wherein said processing means includes a processor for extracting data of the deformed area of said joint based on data of the image stored in said video memory means to make the test decision of said joint based on the data of said deformed area.

20. An apparatus for testing a joint according to claim 14, wherein said processing means includes read means for sequentially reading the content of said video memory means.

21. An apparatus for testing a joint according to claim 20 wherein the image stored in said video memory means is divided into a plurality of lines each having a plurality of picture cells, and said read means reads the data of the image stored in said video memory for one line at a time.

22. An apparatus for testing a joint according to claim 19 wherein the image stored in said video memory means is divided into a plurality of lines each having a plurality of picture cells, and said processing means includes data preparing means for preparing necessary data for one line at a time from the data of the image stored in said video memory means.

23. An apparatus for testing a joint according to claim 22 wherein said processing means produces the data of said joint for one line at a time.

24. An apparatus for testing a joint according to claim 22 wherein said data preparing means produces data of a distance between ends of said joint and a data of a position of the ends of said joint for each line.

25. An apparatus for testing a joint according to claim 13 wherein:
said imaging means sequentially scans each of lines of said image to convert said image to the electric signal; and
said processing means sequentially extracts width data of said joint for each line to select the highest frequency width data as the width of said joint before joining.

26. An apparatus for testing the strength of a joint of a first member and a second member joined by joining means, comprising:

imaging means for imaging said joint on an image plane and converting said image to an electric signal;

measuring means adapted to receive the electric signal from said imaging means for measuring a deformed area of said joint based on said electric signal;

calculation means for calculating a ratio of said area measured by said measuring means to a reference area predetermined for a strength test of the joint;

discrimination means for discriminating if said ratio calculated by said calculation means is within a predetermined area ratio range or not; and decision means for producing a pass signal or a fail signal depending on the discrimination result by said discriminating means.

27. An apparatus for testing the strength of a joint of a first member and a second member joined by joining means, comprising:

imaging means for imaging said joint on an image plane and converting said image to an electric signal;

measuring means adapted to receive said electric signal from said imaging means for measuring a deformed area of said joint based on said electric signal;

comparing means for comparing said deformed joint area measured by said measuring means with a predetermined minimum allowable area and a predetermined maximum allowable area; and decision means for producing a pass signal when the compare result by said comparing means shows that said joint area is no smaller than said minimum allowable area and no longer than said maximum allowable area and producing a fail signal otherwise.

* * * * *